United States Patent [19]
Blubaugh, Jr. et al.

[11] Patent Number: 5,914,026
[45] Date of Patent: *Jun. 22, 1999

[54] IMPLANTABLE SENSOR EMPLOYING AN AUXILIARY ELECTRODE

[75] Inventors: Elmo A. Blubaugh, Jr., Springboro; Alan R. Brunsman, Yellow Springs; Kevin L. Houser, Washington Township, all of Ohio

[73] Assignee: Implanted Biosystems Inc., Kettering, Ohio

[*] Notice: This patent is subject to a terminal disclaimer.

[21] Appl. No.: 08/779,304

[22] Filed: Jan. 6, 1997

[51] Int. Cl.⁶ .................................................. G01N 27/26
[52] U.S. Cl. .......................... 205/792; 204/403; 435/817; 606/32
[58] Field of Search .................... 604/20, 891.1; 204/403; 205/777.5, 779, 792; 606/41, 34, 32; 435/817, 180, 287.9

[56] References Cited

U.S. PATENT DOCUMENTS

| | | | |
|---|---|---|---|
| 4,146,438 | 3/1979 | de Nora et al. | 205/43 |
| 4,401,122 | 8/1983 | Clark, Jr. | 600/358 |
| 4,458,686 | 7/1984 | Clark, Jr. | 600/358 |
| 4,484,987 | 11/1984 | Gough | 205/778 |
| 4,671,288 | 6/1987 | Gough | 600/347 |
| 4,680,268 | 7/1987 | Clark, Jr. | 205/778 |
| 4,703,756 | 11/1987 | Gough et al. | 600/347 |
| 4,721,677 | 1/1988 | Clark, Jr. | 204/403 |
| 4,757,022 | 7/1988 | Shults et al. | 204/403 |
| 4,759,828 | 7/1988 | Young et al. | 205/778 |
| 4,832,009 | 5/1989 | Dillon | 602/58 |
| 4,849,085 | 7/1989 | Debrodt et al. | 204/290 F |
| 4,849,205 | 7/1989 | Hong | 423/644 |
| 4,849,285 | 7/1989 | Dillon | 428/330 |
| 4,859,383 | 8/1989 | Dillon | 264/43 |
| 4,871,366 | 10/1989 | von Recum et al. | 623/11 |
| 4,931,213 | 6/1990 | Cass | 252/507 |
| 4,938,850 | 7/1990 | Rothschild et al. | 205/191 |

(List continued on next page.)

OTHER PUBLICATIONS

Hogson et al. ("Glucose oxidase enzyme electrode: relation between inner membrnae permeability and substrate response", Analytica Chimica Acta, 276(1993), pp. 335–340), 1993.

An Idea Whose Time Has Come, by Shauna S. Roberts, *Diabetes Forecast*, May 1993, pp. 25–27.

Calcium phosphate naturally formed on titanium in electrolyte solution, by Takao Hanawa and Mamoru Ota, *Biomaterials*, 1991, vol. 12, Oct., pp. 767–774.

Potential Applications of Certain Nickel–Titanium (Nitinol) Alloys, by Simon Civjan, Eugene F. Hugen, and Laszlo B. DeSimon, U.S. Army Institute of Dental Research, Walter Reed Army Medical Center, Washington, DC 20212, U.S.A., *J Dent Res,* Jan.–Feb. 1975, vol. 54, No. 1, pp. 89–96.

Comparative Cell Culture Effects of Shape Memory Metal (Nitinol®), Nickel and Titanium: A Biocompatibility Estimation, by J.L.M. Putters, D.M.K.S. Kaulesar Sukul, G.R. DeZeeuw, A. Bijma, P.A. Besselink, *Eur. Surg. Res.,* 1992 month unknown, pp. 378–382.

Elecrochemical and XPS studies of Titanium for biomaterial applications with respect to the effects of hydrogen peroxide, by J. Pan, D. Thierry, and C. Leygraf, *Journal of Biomedical Materials Research,* vol. 28, 113–122 (1994) month unknown, pp. 113–122.

*Primary Examiner*—William H. Beisner
*Assistant Examiner*—Alex Noguerda
*Attorney, Agent, or Firm*—Thompson Hine & Flory LLP

[57] ABSTRACT

An implantable sensor comprising a biocompatible electroconductive case which houses a measuring electrode, a reference electrode, an auxiliary electrode, and an electronic circuit for measuring the response of the measuring electrode where the measuring electrode, reference electrode and auxiliary electrode are not in direct electrical contact with one another is provided. The implantable sensor of the present invention is particularly useful as a glucose sensor, especially when an enzyme-containing membrane is included in the measuring electrode.

19 Claims, 4 Drawing Sheets

U.S. PATENT DOCUMENTS

| | | | |
|---|---|---|---|
| 4,941,201 | 7/1990 | Davis | 455/41 |
| 4,945,125 | 7/1990 | Dillon et al. | 524/427 |
| 4,983,474 | 1/1991 | Doi et al. | 429/59 |
| 4,994,167 | 2/1991 | Shults et al. | 204/403 |
| 5,019,140 | 5/1991 | Bowser et al. | 96/6 |
| 5,030,333 | 7/1991 | Clark, Jr. | 205/777.5 |
| 5,066,683 | 11/1991 | Dillon et al. | 174/59 |
| 5,157,058 | 10/1992 | Dillon et al. | 521/134 |
| 5,205,921 | 4/1993 | Shirkanzedeh | 205/318 |
| 5,260,701 | 11/1993 | Guern et al. | 340/825.54 |
| 5,322,063 | 6/1994 | Allen et al. | 600/347 |
| 5,352,348 | 10/1994 | Young et al. | 205/778 |
| 5,354,390 | 10/1994 | Haszmann et al. | 148/518 |
| 5,362,553 | 11/1994 | Dillon et al. | 442/76 |
| 5,372,133 | 12/1994 | Esch | 600/377 |
| 5,399,250 | 3/1995 | Moon et al. | 204/255 |
| 5,429,895 | 7/1995 | Lian et al. | 429/223 |
| 5,469,846 | 11/1995 | Khan | 600/347 |
| 5,476,589 | 12/1995 | Bacino | 210/500.36 |
| 5,531,878 | 7/1996 | Vadgama et al. | 204/415 | ions 5,914,026

IMPLANTABLE SENSOR EMPLOYING AN AUXILIARY ELECTRODE

BACKGROUND OF THE INVENTION

1. Field of the Invention

The present invention relates to implantable electrochemical sensors and, more particularly to an implantable sensor that utilizes a biocompatible electroconductive case as an auxiliary electrode in a three electrode system.

2. Description of Related Art

The chemical reaction most commonly used in enzyme coupled glucose sensors is the glucose oxidase mediated catalytic oxidation of glucose by atmospheric oxygen to produce gluconolactone and hydrogen peroxide (equation 1):

$$C_6H_{12}O_6 + O_2 + H_2O \rightarrow C_6H_{12}O_7 + H_2O_2 \qquad (1)$$

A typical two electrode electrochemical cell comprises an anode, otherwise known as the measuring electrode, and a cathode, otherwise known as the reference electrode. In the presence of excess oxygen, the quantity of hydrogen peroxide produced in the reaction of Equation 1 will be a direct measure of the glucose concentration. The hydrogen peroxide is detected as it is reoxidized at the measuring electrode which is maintained at a sufficient positive potential to carry out the following reaction (equation 2):

$$H_2O_2 - 2e^- \rightarrow O_2 + 2H^+ \qquad (2)$$

Glucose detection is dependent upon the measurement of electrons removed from hydrogen peroxide in equation (2). The electrode is normally formed from a noble metal such as gold or platinum.

The complementary electrochemical reaction, a reduction, takes place at the cathode or reference electrode, usually a silver/silver chloride electrode, as shown in Equation 3.

$$2AgCl_{(s)} + 2e^- \rightarrow 2Ag + 2Cl^- \qquad (3)$$

For the two electrode electrochemical cell, the magnitude of the current flow for the oxidation of hydrogen peroxide at the measuring electrode must be equal to and balanced by an equivalent flow of current of the opposite sign at the reference electrode. However, in the two electrode electrochemical cell the conventional Ag/AgCl reference electrode's potential can become unstable during operation. The reference electrode potential is a function of the concentration of the silver chloride. If the amount of current flowing through the reference electrode is sufficiently large that the Ag metal or the AgCl solid is exhaustively consumed the potential for the reference electrode will not be constant. As a result, there is a need for a system that limits the amount of the current through the reference electrode such that the Ag metal or AgCl solid is not exhaustively consumed and instability in the reference electrode's potential does not result.

Prior art attempts at solving the problems associated with two electrode systems have employed a third electrode as an auxiliary electrode. U.S. Pat. No. 5,352,348 to Young et al. discloses a glucose sensor that employs a measuring electrode, a silver electrode and a silver/silver chloride electrode.

SUMMARY OF THE INVENTION

The present invention provides an implantable sensor that provides stable reference electrode potential during operation. The implantable sensor comprises a biocompatible electroconductive housing, which functions as an auxiliary electrode, in which a measuring electrode, a reference electrode, a voltage source and an electronic circuit for measuring the measuring electrode's response are housed. For example, the auxiliary electrode reduces the consumption of Ag metal and AgCl solid by reducing the magnitude of the current flowing through the reference electrode and thereby stabilizes the electrode potential.

Accordingly, it is an object of the present invention to provide an implantable sensor that is capable of correcting and preventing instability in the reference electrode's potential during operation.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide an implantable sensor, and more particularly, an implantable sensor having a titanium case. In particular, while the invention is particularly described with respect to a glucose sensor, those skilled in the art will recognize that the principles disclosed herein are applicable in sensors for other analytes.

Figure 1:
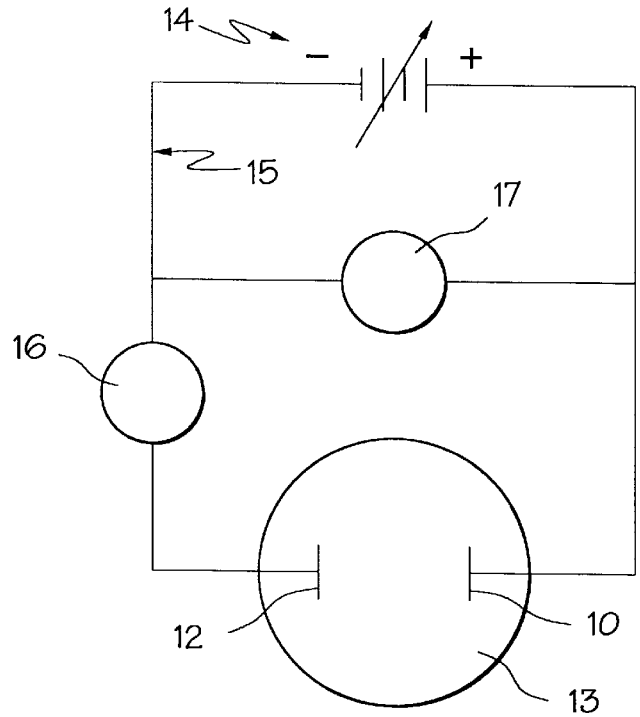
FIG. 1 is a circuit diagram of a typical two electrode electrochemical cell and potentiostat.

FIG. 1 is a circuit diagram of a typical two electrode amperometric electrochemical cell and potentiostat. The two electrode electrochemical cell and potentiostat includes a measuring electrode 10 and a reference electrode 12, preferably a silver electrode and more preferably a Ag/AgCl electrode. The measuring electrode 10 is a platinum anode, which is in contact with an ionically conductive solution 13, for example aqueous, non-aqueous or body fluids. The voltage source 14 is an adjustable voltage source such as a battery and voltage regulating circuit. The voltage source is set to maintain the measuring electrode 10 at a desired potential. In the case of the oxidation of hydrogen peroxide, this potential is of a positive value greater than 0.500 volts, but does not exceed +0.700 volts. This applied potential is versus the reference electrode 12, which is also in physical contact with the ionically conductive solution 13. The hydrogen peroxide gives up electrons to the measuring electrode 10 in the oxidation step. These electrons travel from the measuring electrode 10, via an electronic conductor, generally designated 15, to the reference electrode 12 where they complete the circuit as they are returned to the solution 13 via the reduction of the AgCl solid. As these electrons pass through the conductor, they are measured by an ammeter 16, which allows one to measure the electroactive analyte, hydrogen peroxide. The voltage difference between the measuring and reference electrodes 10 and 12, respectively, is measured by a voltmeter 17.

As previously noted, significant current flow through the reference electrode can result in electrochemical side reactions that can damage a silver electrode. In accordance with this invention, a third or auxiliary electrode, takes the place of the reference electrode in returning the bulk of the current to the aqueous solution. The reference electrode is still in contact with the aqueous solution and a potentiostat senses the electrical potential of this electrode relative to the solution and fixes the auxiliary electrode at a potential so that the auxiliary electrode can act as a "surrogate" for the reference electrode. Because very little current flows through the reference electrode in this arrangement, the reference electrode is not exhausted and a stable reference electrode potential can be maintained.

Figure 2:
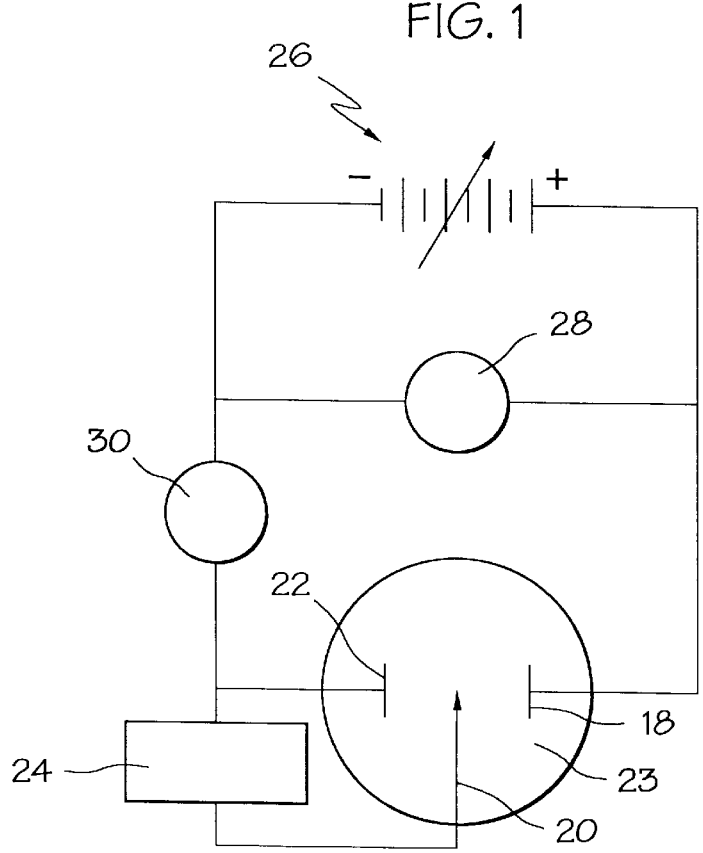
FIG. 2 is a circuit diagram of a three electrode electrochemical cell and potentiostat system in accordance with the present invention.

A three electrode electrochemical cell and potentiostat circuit diagram, in accordance with the present invention, is shown in FIG. 2. The three electrode electrochemical cell and potentiostat includes a measuring electrode 18, which is preferably a platinum anode, a reference electrode 20, which is preferably a silver electrode and, more preferably a Ag/AgCl electrode, and an auxiliary electrode 22. All three electrodes are in contact with an ionically conductive solution 23, for example aqueous, non-aqueous or body fluids. A potentiometer 24 measures the electrical potential between the measuring electrode 18 and the reference electrode 20. The electrical potential of the auxiliary electrode 22 is established by the variable voltage source 26. The voltage difference between the auxiliary electrode 22 and the measuring electrode 18 is measured by a voltmeter 28.

Generally, the operation of the three electrode electrochemical cell and potentiostat is as follows. A certain potential difference between the measuring electrode 18 and the reference electrode 20 is desired, therefore, the variable voltage source 26, is adjusted until the desired potential difference between the measuring electrode 18 and the reference electrode 20 is established. This potential difference is measured by the potentiometer 24. The magnitude of the current observed for that potential difference between the measuring electrode 18 and the reference electrode 20 is measured by an ammeter 30. The measured current is proportional to the concentration of the electroactive analyte. One advantage of an auxiliary electrode is that the amount of current flow between the measuring electrode and the reference electrode in a three electrode system is very small, typically ten orders of magnitude smaller than the current through the measuring electrode and reference electrode in a two electrode system.

Figure 3:
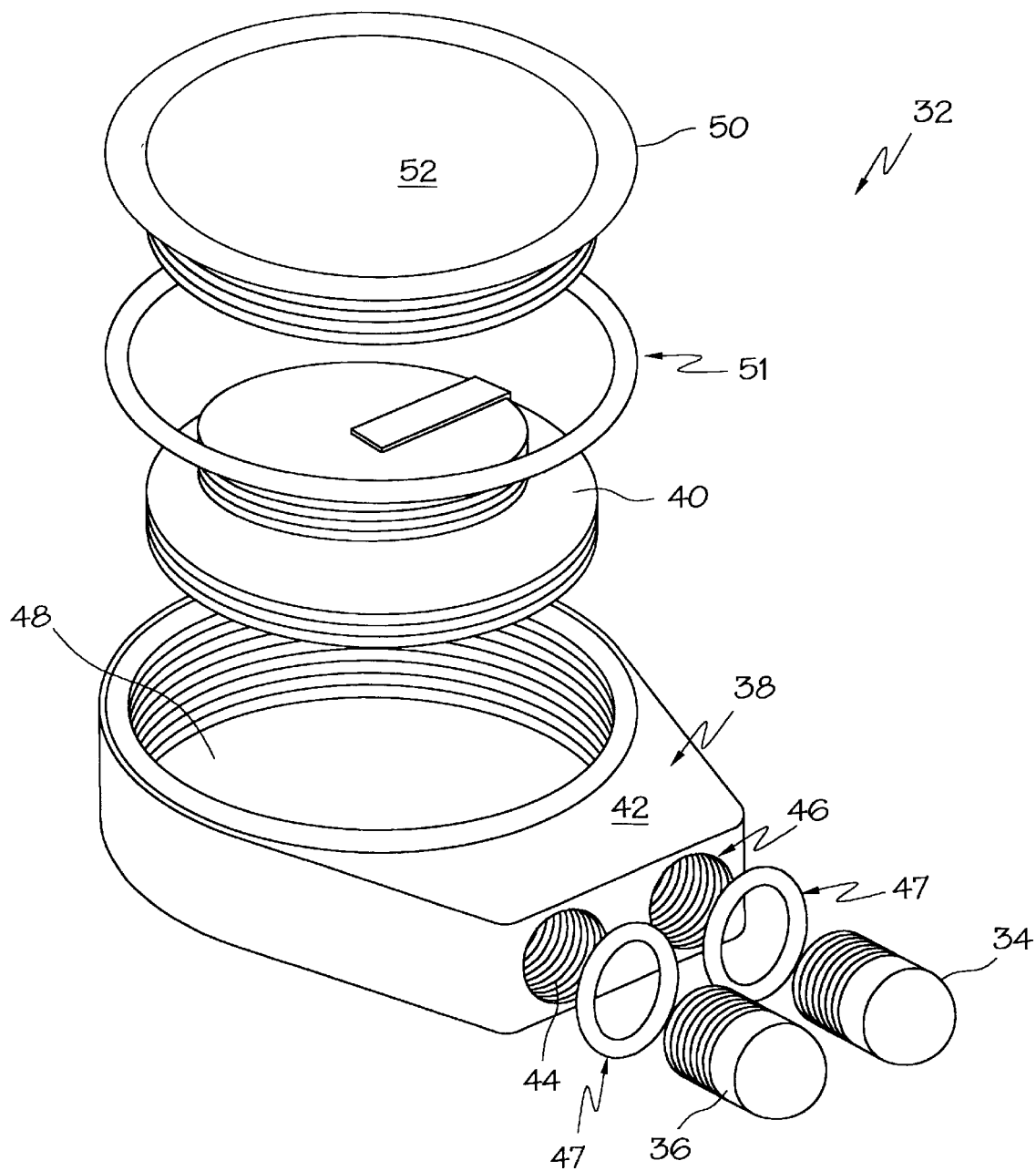
FIG. 3 is an exploded view of an implantable glucose sensor device employing the three electrode electrochemical cell and potentiostat of the present invention.

As shown in FIG. 3, an implantable sensor, such as a glucose sensor, generally designated 32, in accordance with the present invention may be disc shaped, although many other configurations are also possible. The sensor 32 comprises a measuring electrode 34, a reference electrode 36, an auxiliary electrode, generally designated 38, and an electrical circuit 40 for measuring the response of the measuring electrode 34. The measuring electrode 34, reference electrode 36 and auxiliary electrode 38 are not in direct electrical contact with one another. However, it is desirable that the measuring electrode 34, reference electrode 36 and auxiliary electrode 38 form an electric circuit when they contact the ionically conductive solution.

The auxiliary electrode 38 is a case 42 made from a suitable electroconductive biocompatible material, preferably a metal. The case 42 must be made from an electroconductive material so that it can function as the auxiliary electrode 38 within the sensor 32. The preferred electroconductive material is titanium because of its excellent biocompatibility characteristics, its strength and its relatively low cost. Titanium metal is known to possess excellent biocompatibility characteristics with regard to living body tissues. As a result, titanium metal has been frequently used for implants, such as bone, dental and heart pacemakers. Examples of other materials that can be used for the case are graphite/epoxy composite, stainless steel, silver, gold, platinum, and titanium alloys, such as nickel-titanium or nickel-titanium-copper. In addition, the case may be coated with a bicompatible coating of hydroxyapatite or be electrochemically coated with an oxide or carbide coating both of which processes are known in the art.

It is desirable that the case 42 has a large surface area so that the current density of the auxiliary electrode 38 is small. By minimizing the current density of the auxiliary electrode 38, the damage to the living tissue surrounding the implantable sensor 32 can be minimized. The surface area of the case 42 can be in the range of about 10 $cm^2$ to about 60 $cm^2$, preferably in the range of about 15 $cm^2$ to about 45 $cm^2$. It is additionally desirable that the case 42 is chemically inert or unreactive.

The case 42 includes a first port 44 in which the reference electrode 36 is mounted and a second port 46 in which the measuring electrode 34 is mounted. The reference electrode 36 is preferably a silver or silver/silver chloride reference electrode. The measuring electrode 34 is preferably a noble metal anode, more preferably a platinum anode. Generally, the area occupied by the first port 44 is small about 0.1 $cm^2$ to 0.4 $cm^2$. Generally, the area occupied by the second port 46 is small about 0.1 $cm^2$ to 0.4 $cm^2$. The reference and measuring electrodes 36 and 34 are sealed to the case 42 via O-rings, generally designated 47. Alternatively, the case 42 may comprise a port that contains both the reference electrode 36 and the measuring electrode 34 so long as the reference electrode 36 and measuring electrode 34 are not in direct electrical contact (i.e., a short circuit) with one another or with the auxiliary electrode 38.

The case 42 further comprises a compartment 48 that is shaped to receive the electronic circuit 40, for example a circuit board. A lid, generally designated 50, is used to seal the electronic circuit 40 within the case 42 via an O-ring, generally designated 51. The lid 50 can be either a resealable lid 52 or welded into place (not shown). The electronic circuit 40 includes means for transmitting a signal to a receiver located outside the body. Any suitable means for transmitting a signal to a receiver located outside the body can be used. For example, a miniature power supply (not shown), such as a lithium battery, and microelectronics for transmitting a measured signal to a receiver outside of the human body can be used. Transmission of data can be by means of radio waves, sound waves or even by means of modulated light. Although it is also possible to actually have a small wire connection to the sensor 32, this is not favored because of problems with infection at the point that the wire breaches the skin. Examples of other communication/transmitting means are described in U.S. Pat. No. 4,941,201 to Davis and U.S. Pat. No. 5,260,701 to Guern et al., which are incorporated herein by reference. Those skilled in the art will appreciate that other suitable communication means are within the scope of the present invention.

It is desirable that the sensor 32 is implanted beneath the surface of the skin with the second port 46 and the measuring electrode 34 facing towards the underlying layer of muscle. This position allows ready access to the unit for repair or replacement. The sensor 32 can also be implanted so that the second port 46 and measuring electrode 34 face the peritoneal cavity. It is relatively important that the sensor 32 not be directly in contact with the circulatory system so that formation of blood clots does not interfere with the operation. While anticoagulants can be used to prevent clot formation, unless the patient requires anticoagulative therapy for some other reason, it is probably not prudent to require anticoagulation simply for an implantable sensor device.

A successful implantable sensor must make accurate measurements over a prolonged period of time and must be biologically compatible, i.e., not induce attempts by the body to reject the implants. Generally, biological compatibility is not an extremely serious problem for a housing of the sensor device. Implants made of a biocompatible material usually become surrounded by a layer of fibroblasts, but there are generally no episodes of rejection. A number of well-known biologically compatible materials are suitable for fabrication of implantable devices. For example, small implants machined from titanium are easily polished and are well accepted by the human body. A wide range of plastic materials such as teflon are also biocompatible. For experimental purposes more easily machinable materials such as 405 stainless steel may be preferable to titanium and are also well tolerated. It has been found particularly advantageous to use titanium to encase the implantable device of the present invention. The titanium surface can be used as an auxiliary or third electrode for the detection system with the electronics within the case connected so as to maintain the measuring electrode at a constant potential relative to the reference electrode. The use of an auxiliary electrode allows the amperometric current to be carried by the case and, thus, be spread over a large area so that the current density is very low and will cause no biological effects.

The potential for current leakage problems exist with an enclosed titanium device unless the measuring electrode and the reference electrode are electrically isolated from the titanium case which acts as the auxiliary electrode. It has been found that the platinum in glass feed-through technology originally developed for high vacuum applications is an ideal solution to this problem. Briefly, special types of glass that have coefficients of expansion nearly identical to platinum are available from Alberox Corp. A platinum wire may be passed through a bead of such a glass and the bead melted onto the platinum to make a water and gas tight junction. Such an insulator bead can then be potted into a hole drilled through the titanium case using, for example, laser welding. Alternatively, the platinum electrode can be cemented into the port using a nonconductive cement.

Many researchers working on implantable glucose sensors may not appreciate the importance of sensor calibration. Both the enzyme mixture and the measuring electrode may change with time. Also, the microcirculation around the sensor may change so that the effective concentration of oxygen changes. Unless the enzyme mixture response has the same slope at all possible oxygen concentration, this could significantly change the accuracy of the glucose measurements. Laboratory instruments are calibrated by being given analytes with known characteristics and then adjusting the instrument's output to match the known analyte. Unfortunately, it is not possible to easily expose an implanted sensor to a known concentration of glucose.

Considering that the implanted sensor is measuring a body compartment that is in equilibrium with the blood, blood glucose measurements can be used to effect calibration. If the patient takes a series of blood glucose measurements over time, these can be plotted against sensor output to develop a time constant for sensor response. Thereafter, blood glucose measurements can be used to automatically calibrate or adjust the implanted sensor.

Even though the device of the present invention is preferably implanted in a site away from direct blood circulation to avoid clotting problems, leukocytes will migrate out of the circulatory system to congregate around any "foreign" body. This leukocyte accumulation may damage the membrane or compromise the accuracy of the glucose readings. However, this problem can be largely avoided by incorporating an effective amount of an anti-inflammatory, anti-leukocyte compound into the enzyme mixture. One example is the addition of hydrocortisone, or similar cortical steroids such as cortisone and prednisolone, at about 0.1 to 1.0% by weight. These steroids can be dispersed in the aqueous phase of the enzyme mixture where they gradually dissolve and very slowly diffuse out through the outer membrane keep the surrounding area free from attack by leukocytes.

In a preferred embodiment of the invention, the measuring electrode 34 includes an enzyme-containing membrane having a semi-interpenetrating polymer network of fibrillated polytetrafluoroethylene and a silicon compound, wherein the network is infiltrated with an enzyme, preferably glucose oxidase. This enzyme-containing membrane is described in U.S. patent application Ser. No. 08/769,863, filed on Dec. 19, 1996, (Attorney Docket No. 594936.002), which is incorporated herein by reference.

Figure 4:
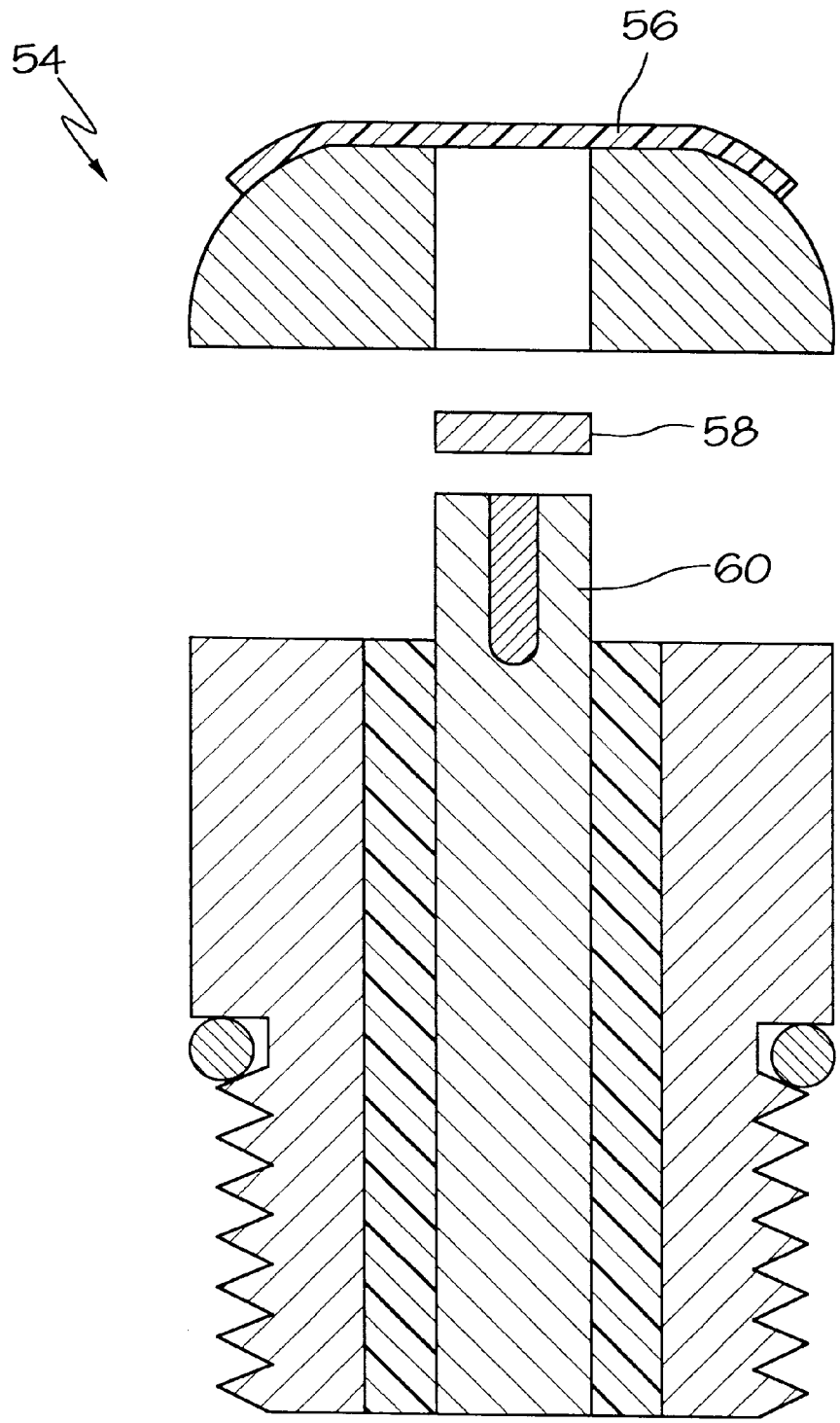
FIG. 4 is an exploded view of a schematic diagram of a glucose sensor employing an enzyme-containing membrane in accordance with the present invention.

FIG. 4 illustrates one embodiment of the invention in which a glucose sensor employs an outer membrane 56 and an enzyme-containing membrane 58, and a measuring electrode 60. The enzyme-containing membrane 58 is disposed between the outer membrane 56 and the electrode 60. The measuring electrode can be any suitable electrode that is capable of detecting and measuring hydrogen peroxide. Preferably, the electrode is a noble metal electrode, more preferably a platinum electrode. It is desirable that the surface of the electrode 60 is maintained electro-active to maximize the effectiveness of the glucose sensor.

In order to achieve accurate measurements of glucose (or other analytes) levels within the blood, the concentration of oxygen at the site of glucose oxidation must be greater than or equal to the glucose concentration at the site of glucose oxidation such that the glucose is the limiting factor in the oxidation reaction rather than the oxygen. To achieve and maintain this stoichiometric relationship at the site of glucose oxidation, the glucose concentration must be restricted and oxygen transport to the site of glucose oxidation must be enhanced. In operation, glucose and oxygen contained within the body tissues of a subject come into contact with the outer membrane 56 of the glucose sensor 54. The outer membrane 56 provides greater restriction to glucose than to oxygen and thus, reduces the concentration of glucose flowing through the outer membrane 56. The function of the outer membrane 56 is to affect the concentrations of glucose and oxygen such that after the glucose and oxygen have passed through the outer membrane 56, the concentration of oxygen is preferably greater than or equal to the concentration of glucose. By doing so, the outer membrane 56 establishes the stoichiometric relationship required for the glucose oxidation reaction.

After the stoichiometric relationship between the oxygen and the glucose has been established by the outer membrane 56, this stoichiometric relationship must be maintained at the sites of glucose oxidation, namely the enzymes contained within the enzyme-containing membrane 58. Maintaining this stoichiometric relationship at the enzymes is facilitated by the semi-interpenetrating polymer network and its enhancing effects on oxygen transport. Furthermore, the enzyme-containing membrane 58 creates a tortuous path for the glucose in its attempt to pass through the membrane, however, it does not restrict the flow of glucose to the enzymes. This added restrictive control on glucose and the enhanced oxygen transport to the enzymes, such that localized concentrations of oxygen are formed, insures that the stoichiometric relationship is maintained at the enzymes. Therefore, at a particular enzyme, the concentration of oxygen at the enzyme is greater than or equal to the concentration of glucose at the enzyme. As a result of the stoichiometric relationship between oxygen and glucose at the enzymes, oxygen does not act as the limiting factor in the glucose oxidation reaction. Thus, the hydrogen peroxide generated during the glucose oxidation corresponds to the glucose present at the enzyme. Current flow representative of oxidation of hydrogen peroxide at the anode must be measured relative to a reference electrode so that a complete circuit is formed. The reference electrode is commonly provided by a silver or silver/silver chloride electrode in electrical contact with the body fluids.

The outer membrane 56 is preferably a polycarbonate but may be made of any other suitable solid porous or permeable material. The outer membrane reduces the rate of mass transport of the glucose through the membrane and yet does not interfere with the rate of mass transport of the oxygen through the membrane. Thus, the outer membrane 56 provides the restrictive control for the glucose. The outer membrane 56 also prevents catalase, an enzyme that destroys hydrogen peroxide, and other large molecules from passing through the membrane. The pore size and thickness of the outer membrane are selected to insure that the passage of glucose through the outer membrane is sufficiently hindered in comparison to the passage of oxygen. In general, the thicker the membrane and the smaller the pore size, the more the passage of glucose will be hindered. In implantable glucose sensors, the outer membrane 56 must be made from a suitable biocompatible material.

One example of a membrane which is useful as the outer membrane 56 and which is commercially available is a polycarbonate membrane available from Poretics Corp. of Livermore, Calif. This membrane is available and employed in pore sizes of about 0.01 to 0.1 micron and pore densities of about $4 \times 10^8$ to $6 \times 10^8$.

The enzyme-containing membrane 58 comprises a semi-interpenetrating polymer network, made of fibrillated polytetrafluoroethylene (PTFE) and a silicon compound. This membrane is commercially available and a method for making this membrane is described in U.S. Pat. Nos. 4,945,125 and 4,832,009, and Dillon, *Silicone and Poly (tetrafluoroethylene) Interpenetrating Networks,* 1994, p. 393, which are incorporated herein by reference. The membrane can range in thickness from about 5 to 50$\mu$. The membrane typically contains about 10 to 40% by volume of the silicon compound or elastomer. The porosity of the enzyme-containing membrane is from about 25% to about 55%.

The term "semi-interpenetrating polymer network" is used herein to refer to membranes prepared by the methods described in either of the aforementioned patents to Dillon and their functional equivalents. The method for making the semi-interpenetrating polymer network as described in U.S. Pat. No. 4,945,125 comprises the steps of: (1) intimately blending a mixture of a major amount of unsintered and unfibrillated particulate polytetrafluoroethylene dispersion resin (commercially available from E. I. du Pont de Nemours & Co., Inc., under the designations TEFLON® 6 and 6C and by Imperial Chemical Industries as FLUON® CD1, CD123 and CD525) and minor amounts of (A) a hydrocarbon liquid and (B) an addition curable silicone composition consisting essentially of a polydiorganosiloxane having alkenyl unsaturation, an organohydrogenpolysiloxane crosslinking agent, a catalyst for promoting crosslinking of the polysiloxane, and an inhibitor for the catalytic reaction; (2) forming the blend into an extrudable shape; (3) biaxially extruding the blend through a die into a shaped extrudate product having a randomly fibrillated structure; and (4) evaporating the hydrocarbon liquid, and activating the catalyst so as to generate a cured silicone elastomer and polytetrafluoroethylene semi-interpenetrating polymer network comprising the fibrillated extrudate structure.

Another method for making a semi-interpenetrating polymer network as described in U.S. Pat. No. 4,832,009 comprises the steps of: (1) blending polyorganosiloxane (commercially available from Dow Corning Corporation under the name SILASTIC® MDX4-4210) with a catalyst for promoting crosslinking of the polysiloxane in a 10:1 ratio; (2) mixing the blend with kerosene (commercially available from Fisher Scientific); and (3) applying the mixture to a substrate of expanded polytetrafluoroethylene film (commercially available from Tetratec Corporation of Feasterville, Pa.) by means of a spray apparatus.

Figure 5:
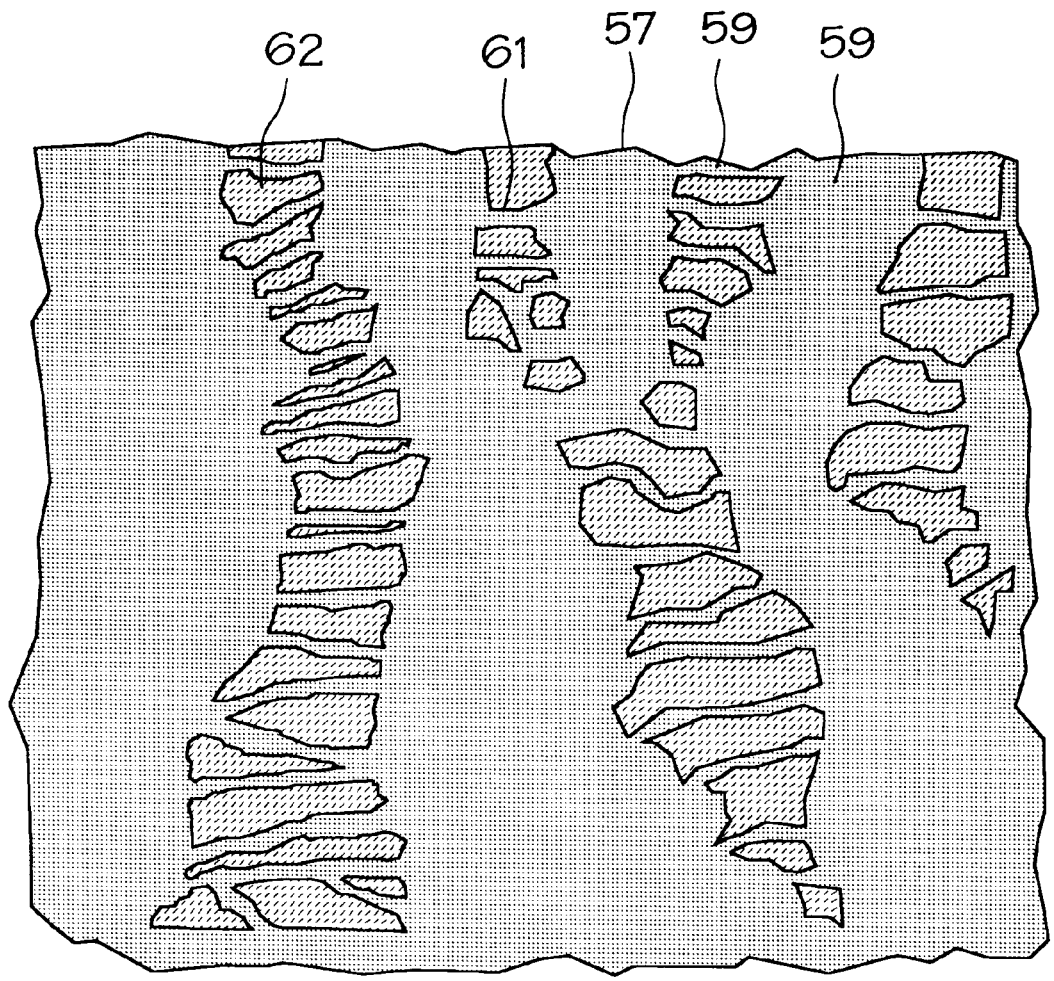
FIG. 5 is a schematic representation of a portion of an enzyme-containing membrane in accordance with the present invention.

Preferably, the silicon compound in the semi-interpenetrating polymer network is a cross-linked polyorganosiloxane, more preferably polydimethylsiloxane. The silicon compound facilitates the transport of oxygen to the sites of glucose oxidation. The semi-interpenetrating polymer network of fibrillated PTFE provides a porous membrane. The porosity of the membrane makes it possible to infiltrate it with the enzyme thus forming the enzyme-containing 20 membrane 58, FIG. 4, a portion of which is represented by the schematic representation in FIG. 5. As shown in FIG. 5, the semi-interpenetrating network, generally designated 59, is a network of nodes 57 and fibrils 61 infiltrated with the enzyme 62. It has been found that by utilizing this semi-interpenetrating network, which has a very high affinity for oxygen, oxygen transport to the enzyme, the site of glucose oxidation, is increased resulting in an oxygen concentration that will be greater than or equal to the concentration of glucose at the enzyme. Less thick membranes improve the speed of detection or response. An example of a commercially available membrane that can be used in accordance with the invention is White Silon #320 from Biomed Sciences, Inc.

To facilitate the infiltration of the enzyme into the semi-interpenetrating network, it is desirable to treat the semi-interpenetrating polymer network with a surfactant. The surfactant renders the membrane hydrophilic. Preferably, the surfactant is a nonionic surfactant, more preferably, methyl terminated poly(dimethylsiloxane-b-ethylene oxide). However, it is anticipated that other surfactants can be used and especially surfactants with a silicon moiety and a hydrophilic moiety.

It is desirable that the enzyme is free from catalase activity, has a relatively long life, is very active and is a pure concentrate to maximize the effectiveness of the glucose sensor. Preferably, the enzyme is an oxidase, more preferably glucose oxidase (E.C. 1.1.3.4). Other useful enzymes have already been mentioned. It is also within the scope of the invention to use more complex systems employing a combination of enzymes. For example, enzyme systems are known in which a first enzyme reacts with an analyte to provide an intermediate which reacts with a second enzyme to produce the chemical species that is detected at the electrode.

The speed of oxygen diffusion through a barrier is controlled by the thickness of the barrier and by the amount of oxygen that can dissolve through a unit thickness of the barrier. That is, making the barrier thinner, i.e., bringing the analyte containing fluid closer, or making the barrier dissolve more oxygen will increase the rate of oxygen diffusion. Therefore, the enzyme-containing membrane 58 should be made as thin as feasible to maximize the rate of oxygen movement into the glucose sensor 54.

The enzyme can be immobilized within the interpenetrating network using a number of techniques. Preferably the enzyme is mixed with other proteins and crosslinked to form an enzyme gel as described below. However, other immobilization techniques may also be useful. For example, the silicon compound could be functionalized such that the enzyme could be covalently linked to the interpenetrating network. The enzyme can also be compounded with matrix formers, such as polymers, film-formeres or binders.

In one embodiment of the invention, the enzyme-containing membrane can be prepared by dissolving the enzyme in a solution of a carrier protein, such as an albumin, i.e., bovine serum albumin (BSA), and human albumin, or gelatin, in a suitable buffer such as 0.20 M sodium acetate buffer (pH=5.00). The enzyme concentration will vary depending upon the activity of the enzyme. Glucose oxidase is dissolved in the mixture at about 5 to 50% by weight. Amounts of alternative enzymes can be determined empirically based upon the activity of the particular enzyme. The enzyme mixture is applied to the semi-interpenetrating network and uniformly infiltrated into the semi-interpenetrating network by gently spreading the enzyme mixture on the membrane and rubbing with a smooth blunt spatula, thus resulting in an enzyme-containing membrane. Glutaraldehyde/acetate buffer is applied to the semi-interpenetrating network after the enzyme has been applied to crosslink the enzyme.

An alternative method may be used for infiltration of the enzyme into the semi-interpenetrating polymer network if the stabilized gel is to be based on a cross-linked protein gel. In this method, a suitable soluble carrier protein, such as an albumin, i.e., bovine serum albumin (BSA), and human albumin, or gelatin, at about 1 to 15% by weight final concentration is dissolved in a suitable buffer such as 0.2 M sodium acetate buffer, and an enzyme such as glucose oxidase is dissolved in the mixture at about 1% to 5% by weight final concentration. Sufficient purified glutaraldehyde as an aqueous 2.5% solution is added to dilute the protein solution to the correct final concentration. The final glutaraldehyde concentration following dilution is preferably between 0.1 and 1% and more preferably about 0.6%. This mixture is swirled briefly to mix and is then poured onto the membrane supported on glass plate and spread with a glass rod. Within a few hours a uniform layer of enzyme gel is formed. This gel is stored in a humidified atmosphere to prevent dehydration of the gel.

The incorporation of the novel enzyme-containing membrane into the glucose sensor of the present invention provides a glucose sensor that accurately measures glucose levels in extremely low oxygen environments such as 2% oxygen. In addition, the enzyme-containing membrane shows no decrease in response for at least about 2½ months. In fact, the enzyme-containing membrane's performance has been observed to improve as it ages.

The glucose sensor of the present invention comprises a measuring electrode, preferably a platinum anode, that is in contact with an aqueous fluid to be measured, e.g., the glucose-containing solution. A voltage source maintains the measuring electrode at a proper potential (here a positive potential to oxidize hydrogen peroxide). A reference electrode is also in contact with the glucose solution. The electrons removed from hydrogen peroxide at the measuring electrode flow through a conductor to the reference electrode where they complete the circuit by being returned to the aqueous solution. As the electrons pass through the conductor they are measured by an ammeter thus allowing the hydrogen peroxide to be quantitated.

It is apparent that all electrical contact with the solution must be made by means of the two electrodes. If there are other conductive pathways, current leakage would produce spurious current flows resulting in improper measurements. Where the electrodes simply dip into the aqueous solution, air insulates the remainder of the circuit and prevents current leaks. In implanted devices, the danger of current leaks becomes very great. As will be elaborated below, the present invention seals all of the electrical components in a small implantable package. In this case it is absolutely essential that the seal be water tight to avoid current leaks and to avoid water damage to the electronics.

An additional problem with implanted electrodes is that a significant current flow through the reference electrode often results in electrochemical side reactions that can damage a silver electrode and may also be toxic to the living tissue around the device. The solution to this problem seems to be the use of a third or auxiliary electrode. A third or auxiliary electrode, usually of a larger area and non-reactive material, takes the place of the reference electrode in returning the bulk of the current to the aqueous solution. The reference electrode is still in contact with the aqueous solution and a potentiostat senses the electrical potential of this electrode relative to the solution and fixes the auxiliary electrode at this potential so that the auxiliary electrode can act as a "surrogate" for the reference electrode. Be cause very little current flows through the reference electrode in this arrangement, there are no side reactions to damage the reference electrode or the surrounding living tissue.

A subject's glucose level can be determined by using the glucose sensor of the present invention by situating the glucose sensor within the subject and calculating the glucose level from the measuring electrode's response. For external use, the glucose level of a sample of blood from a subject can be determined by using the glucose sensor of the present invention and calculating the glucose level from the measuring electrode's response.

Another serious impediment to long term sensor implants is that of microbial contamination by bacteria and fungi, etc. While microbes may directly destroy the glucose metabolizing enzyme, it is also likely for them to disrupt the glucose measurement by producing catalase or peroxidases which consumes the hydrogen peroxide before it can react with the electrode surface. The incorporation of antifungals or wide spectrum antibiotics into the enzyme mixture will largely prevent microbial interference. For example, gentamicin and/or penicillin, at about 0.1 to 0.8% percent by weight, and/or other broad spectrum antibiotics can be incorporated into the enzyme mixture to prevent bacterial interference.

The outer membrane 56 is generally believed to protect the glucose oxidase from various proteases. However, in the experiments leading to the present invention, it was discovered that stabilized glucose oxidase is not readily attacked by the common proteolytic enzyme trypsin. Therefore, trypsin may be incorporated in the outer membrane as an antiproteolytic enzyme to help destroy other proteolytic enzymes that might be produced by microorganisms, etc.

Stability of the enzyme mixture of the present invention can also be improved by the addition of antioxidants and/or free radical trapping agents. Vitamin E, which is also an oxygen solvent, can be incorporated into the enzyme mixture as can any of a number of "preservatives" such as various parabens, BHT (butylated hydroxy toluene) and its analogs, and/or superoxide dismutase.

In another embodiment of the glucose sensor employing the enzyme-containing membrane, a third membrane is situated between the enzyme-containing membrane and the electrode, i.e., so as to sandwich the enzyme containing membrane between the outer membrane and this third membrane. The function of the third membrane is to exclude compounds such as ascorbic acid and acetaminophen from interfering with the analysis. A cellulose acetate membrane can be used for this third membrane. See U.S. Pat. Nos. 3,979,274 and 4,073,713 to Newman.

Those skilled in the art will appreciate that various adaptations and modifications of the just-described preferred embodiments can be configured without departing from the scope and spirit of the invention. Therefore, it is to be understood that, within the scope of the appended claims, the invention may be practiced other than as specifically described herein.

EXAMPLE 1

Preparation of Enzyme-Containing Membrane

Commercially available polytetrafluoroethylene and polydimethylsiloxane semi-interpenetrating polymer network membranes, also known as White Silon #320 (Bio Med Sciences, Inc.), were removed from their release liner, as membrane strips 2" by 3" and were rinsed with deionized water and ethanol. These membranes were stored in a bottle of sterilizing 70% Ethanol/deionized water, until they were used for enzyme studies.

The membranes were removed from their storage bottle and placed on a 4" by 4" glass plate. The strips of membrane were stretched out on a glass plate and blotted dry. Then approximately, 10 to 20 drops of a nonionic surfactant, Dimethylsiloxane-ethylene oxide copolymer, 20 cs., United Chemical Technologies, Inc.), were deposited on the membrane strips and the drops of surfactant were rubbed into the membrane structure with a smooth and blunt spatula. The membrane appearance turned translucent, which differed from it's original white opalescence. The strips of membrane were placed in a container and a 5% aqueous solution of the nonionic surfactant was poured into the container and the membranes were soaked for a period of at least 24 hours. The membranes are removed from the soaking solution and rinsed with deionized water until the membrane did not feel slippery. The membranes were again placed on a glass plate and blotted dry and then allowed to dry in the ambient laboratory environment.

The enzyme gelling solution for infiltration into the membranes was formulated with Glucose Oxidase, Type VII from Aspergillus Niger, EC 1.1.3.4 (Sigma Chemical Co.) and Bovine Serum Albumin, Fraction V Powder (Sigma Chemical Co.). About 0.1000 grams of Glucose Oxidase and 0.400 grams of Bovine Serum Albumin are mixed together in a 0.20 M Sodium Acetate (pH=5.00) (Sigma Chemical Co.) buffer, until they both dissolve in the acetate buffer (volume=7.5 ml). In a separate vial, a solution of 1.0 ml 25% Glutaraldehyde, Grade 1 (Sigma Chemical Co.) is mixed with 9.0 ml of acetate buffer (pH=5.00), which results in a 2.5% Glutaraldehyde/acetate buffer. A 2.5 ml aliquot of this 2.5% Glutaraldehyde/acetate buffer is removed and set aside for use later in crosslinking the enzyme gel in the pores of the modified White Silon #320 membrane. About 2.5 ml of the Glucose Oxidase/Bovine Serum Albumin solution is placed on the modified White Silon #320 membrane (one of the 2" by 3" strips of membrane on a glass plate) via a pipette. These drops wicked into the membrane and the solution was uniformly dispersed in the membrane by gently rubbing the membrane with a smooth blunt spatula. A visual judgement is made of the membrane after the Glucose Oxidase/Bovine Serum Albumin (GOD/BSA) is allowed to dry for about 30 minutes. If the solution of GOD/BSA has penetrated the pores of the membrane and evenly deposited within the pores the membrane will look a yellow translucent color. If there are gaps or incomplete deposition there will be spots of the membrane, which will not be colored yellow. After this visual inspection, about 0.8 ml of the 2.5% Glutaraldehyde/acetate buffer was added to the membrane as droplets and this solution was spread over the entire membrane area, in order to ensure even distribution of the cross-linking and immobilizing agent, Glutaraldehyde. The glass plate holding the GOD/BSA embedded White Silon #320 membrane was placed in a plastic zip lock bag (Glad), with a small amount of the 2.5% Glutaraldehyde solution in an open vial and left enclosed in this plastic bag for a period of 60 hours. The fully crosslinked and immobilized enzyme gel membrane was removed from this plastic bag and placed in another bag, which contained Gomori Buffer soaked cotton gauzes and the top of the bag was zipped shut. The buffer soaked gauzes maintained a humid environment for the enzyme gel membrane in the closed plastic bag, and the closed bag was marked with the appropriate date and laboratory notes and placed in a refrigerator for storage.

The membrane prepared as described above was very elastic and flexible, so long as it was wet. If the membrane was allowed to dry out it would become very brittle. However, with the addition of a water(buffer) the membrane became elastic once again. This drying out and rehydration cycle seems to be totally reversible, in that no loss of enzyme activity is noted. Also, there is no observable degradation of the mechanical properties for this enzyme embedded membrane. The thickness of membranes produced by the above procedure was in the range of from about 50 microns to 65 microns.

EXAMPLE 2

Preparation of Glucose Sensor

A glucose sensor in accordance with the present invention was prepared by punching a small disc (a #16 needle, about 0.1 mm) of the enzyme-containing membrane, prepared in Example 1 above. This disc is placed in a small vial with a milliliter of Gomori buffer. An electrode collar is solvent glued (methylene chloride) to an outer membrane made of polycarbonate. This assembly was set aside to dry, with the outer membrane lying on the bottom. After about 30 minutes, a small drop of Gomori buffer was placed in the "well" of the electrode collar. The small disc of enzyme-containing membrane was placed in the well and allowed to settle to the bottom of the well. This operation takes patience, in that, the disc of enzyme-containing membrane may need to be pushed under the meniscus of the drop of buffer in the well of the electrode collar. A platinum/ceramic electrode was glued into a titanium electrode port. This assembly was placed at the top of the well and the Platinum/Ceramic electrode is press fitted into the electrode collar. The platinum/ceramic electrode is pushed into the electrode collar until it is seated flush with the top of the titanium electrode port. The enzyme-containing membrane disc was then clearly visible under the outer membrane, as a yellow disc.

Having described the invention in detail and by reference to preferred embodiments thereof, it will be apparent that modifications and variations are possible without departing from the scope of the invention defined in the appended claims.

What is claimed is:

1. A sensor for implanting in the body of a patient comprising a biocompatible electroconductive case, a voltage source, a measuring electrode, and a reference electrode; the case, the voltage source, the measuring electrode and the reference electrode being associated in an electrical circuit in which the case functions as an auxiliary electrode, wherein the measuring electrode includes an enzyme-containing membrane having a semi-interpenetrating polymer network of fibrillated polytetrafluoroethylene and a silicon compound, wherein the network is infiltrated with an enzyme.

2. The sensor of claim 1 wherein said measuring electrode is a platinum anode.

3. The sensor of claim 2 wherein said reference electrode is a silver electrode.

4. The sensor of claim 2 wherein said reference electrode is a silver/silver chloride electrode.

5. The sensor of claim 2 wherein said case is titanium.

6. The sensor of claim 5 wherein the electronic circuit includes a potentiostat for sensing the potential difference between the reference electrode and the measuring electrode.

7. The sensor of claim 5 wherein the case includes a first port containing the reference electrode and a second port containing the measuring electrode.

8. The sensor of claim 5 wherein the electrical circuit further includes means for transmitting a signal to a receiver located outside the body.

9. The sensor of claim 5 wherein the case includes a port containing the reference electrode and the measuring electrode.

10. The sensor of claim 1 wherein the measuring electrode, the reference electrode and the case, when in contact with an ionically conductive solution complete an electric circuit.

11. A method for detecting the glucose level in a patient comprising:

implanting a glucose sensor including biocompatible electroconductive case, a voltage source, a measuring electrode, and a reference electrode; the case, voltage source, measuring electrode and reference electrode being associated in an electrical circuit in which the case function as an auxiliary electrode, wherein the measuring electrode includes an enzyme-containing membrane having a semi-interpenetrating polymer network of fibrillated polytetrafluoroethylene and a silicon compound, wherein the network is infiltrated with an enzyme.

12. The method of claim 11 wherein the measuring electrode is a platinum anode.

13. The method claim 12 wherein the reference electrode is a silver electrode.

14. The method claim 13 wherein said reference electrode is a silver/silver chloride electrode.

15. The method claim 13 wherein the case is titanium.

16. The method of claim 15 wherein the electronic circuit includes a potentiostat for sensing the potential difference between the reference electrode and the measuring electrode.

17. The method of claim 16 wherein the case includes a first port containing the reference electrode and a second port containing the measuring electrode.

18. The method of claim 16 wherein the electronic circuit further includes means for transmitting a signal to receive located outside the body.

19. The method of claim 16 wherein the case includes a port containing the reference electrode and the measuring electrode.

* * * * *

UNITED STATES PATENT AND TRADEMARK OFFICE
CERTIFICATE OF CORRECTION

PATENT NO. : 5,914,026
DATED : June 22, 1999
INVENTOR(S) : Elmo A. Blubaugh, Jr., et al It is certified that error appears in the above-indentified patent and that said Letters Patent is hereby corrected as shown below:

Col. 14, line 36 (claim 18), "to receive"

should be -- to a receiver --.

Signed and Sealed this

Ninth Day of November, 1999

Attest:

Attesting Officer

Q. TODD DICKINSON

Acting Commissioner of Patents and Trademarks